(12) United States Patent
Li et al.

(10) Patent No.: US 9,532,711 B2
(45) Date of Patent: Jan. 3, 2017

(54) AFFECTIVE BANDWIDTH MEASUREMENT AND AFFECTIVE DISORDER DETERMINATION

(71) Applicant: Beijing University of Technology, Beijing (CN)

(72) Inventors: Mi Li, Beijing (CN); Shengfu Lv, Beijing (CN); Gang Wang, Beijing (CN); Ning Zhong, Beijing (CN)

(73) Assignee: Beijing University of Technology, Beijing (CN)

( * ) Notice: Subject to any disclaimer, the term of this patent is extended or adjusted under 35 U.S.C. 154(b) by 41 days.

(21) Appl. No.: 14/731,928

(22) Filed: Jun. 5, 2015

(65) Prior Publication Data

US 2015/0289761 A1    Oct. 15, 2015

Related U.S. Application Data

(63) Continuation of application No. PCT/CN2014/086011, filed on Sep. 5, 2014.

(30) Foreign Application Priority Data

Apr. 20, 2014 (CN) .......................... 2014 1 0148099
Sep. 1, 2014 (CN) .......................... 2014 1 0440520

(51) Int. Cl.
*A61B 3/00* (2006.01)
*A61B 3/10* (2006.01)
(Continued)

(52) U.S. Cl.
CPC ................ *A61B 3/112* (2013.01); *A61B 3/113* (2013.01); *A61B 5/165* (2013.01); *A61B 5/1105* (2013.01)

(58) Field of Classification Search
CPC ..... A61B 5/0002; A61B 5/16; A61B 18/1492; A61B 3/032; A61B 3/1015; A61B 3/103; A61B 3/14; A61B 3/113; A61B 3/1225; A61B 3/024; A61H 5/00; G06Q 30/0203; H04N 21/44222; H04N 60/33; H04N 21/25891
(Continued)

(56) References Cited

U.S. PATENT DOCUMENTS

2007/0066916 A1* 3/2007 Lemos ................... A61B 3/113
600/558
2011/0301433 A1 12/2011 Sadowsky et al.

FOREIGN PATENT DOCUMENTS

WO    WO 2013102768    7/2013

* cited by examiner

*Primary Examiner* — Dawayne A Pinkney
(74) *Attorney, Agent, or Firm* — Tian IP & Technology, LLC.

(57) ABSTRACT

The present disclosure relates to methods for measuring affective bandwidth of a subject (e.g., a human) and determining depression determination of the subject. The affective bandwidth measurement may include the following operations. For example, the subject may watch positive neutral and negative pictures for 8-10 seconds, respectively. Information for all fixation points may be obtained using an eye movement tracking device. Pupil diameter sizes of the subject while watching the positive, neutral and negative picture tasks may be calculated, and the affective bandwidth may be calculated. The affective bandwidth may include positive affective bandwidth (positive-neutral), negative affective bandwidth (negative-neutral) and positive-negative affective bandwidth (positive-negative) of the subject.

1 Claim, 6 Drawing Sheets

(51) Int. Cl.
*A61B 3/02* (2006.01)
*A61B 13/00* (2006.01)
*A61B 3/11* (2006.01)
*A61B 3/113* (2006.01)
*A61B 5/16* (2006.01)
*A61B 5/11* (2006.01)

(58) Field of Classification Search
USPC ................. 351/246, 200, 203, 205, 206,
209–211,351/221–223; 600/300, 558;
358/84; 725/9–10, 725/12–13; 128/898;
705/7.32
See application file for complete search history.

AFFECTIVE BANDWIDTH MEASUREMENT AND AFFECTIVE DISORDER DETERMINATION

CROSS REFERENCE TO RELATED APPLICATION

This application is a continuation application of International application number PCT/CN2014/086011, filed Sep. 14, 2014, titled "a Method for Affective Bandwidth Measurement and Affective Disorder Determination," which claims the priority benefit of Chinese Patent Application No. 201410148099.X, filed on April, 2014, which is hereby incorporated by reference in its entirety. This application also claims priority to Chinese Patent Application No. 201410440520.4, filed on Sep. 1, 2014, titled "a Method for Affective Bandwidth Measurement and Affective Disorder Determination," which is hereby incorporated by reference in its entirety.

TECHNICAL FIELD

The present disclosure relates to a method for measuring affective bandwidth of subject and determining an affective disorder of the subject.

BACKGROUND

Previous affective recognition technologies have primarily been used in studies such as recognition of different types of emotions (e.g., pleasure, sadness and fear) based on the different affective recognition (e.g., voice and face). However, most methods cannot recognize and quantify the same type of affective recognitions in terms of the level of pleasure (i.e., extremely pleased vs. relatively pleased) or the scope of pleasure.

In the field of cognitive psychology, affective experience is measured by presenting pictures of different types of emotions to a subject. The level of pleasure is measured on a scale of 1 to 9, with 9 being the most pleasant and 1 being the least pleasant. The subject selects the level that best depicts the affect induced by the pictures. This method can be used to quantify an emotions of the subject, which is influenced by the subjectivity of the subject with a certain level of uncertainty.

Studies have shown that, the visual stimulation of positive emotions, such as joy and happiness, induces pleasant emotions, indicated by the expansion of the diameter of the pupils of the subject. In contrast, the visual stimulation of negative emotions, such as sorrow and fear, induces unpleasant emotions, indicated by the contraction of the diameter of the pupils of the subject. Therefore, the expansion and contraction of the pupils of a subject serves as an objective indicator of changes of emotions of the subjects.

Affective disorder primarily is characterized as moodiness, deficiency of pleasurable feelings and feeling of depression. Currently, auxiliary scales (such as the Beck scale and the self-rating affective disorder scale) have primarily been used for the determination and estimation of affective disorder, and brain waves and eye movement indexes are also used in determination estimations; however, these determination and estimations are not directly associated with the affective experience due to the shortage of affective indexes directly associated with mood. Therefore, the recognition rate and accuracy of affective injuries is not high. The affective width describes the affective change, and the positive affective bandwidth will be remarkably narrowed, thereby decreasing the affective change range and deficiency of the affective experience induced through external positive emotion information in the case of gloomy mood and the deficiency of pleasurable feelings. Hence, mood disorders such as the deficiency of pleasurable feelings and black moods can be induced. However, affective deficiency will induce negative cognitive schema, resulting in negative cognitive deviation to external information. This tends to perform cognitive processing in the negative psychology for non-negative (positive or neutral) visual stimulation. Therefore, experiences and affective disorder of a normal person are different from external positive and negative affective stimulation such that the positive emotion experience of the affective disorder is smaller than that of the normal person.

SUMMARY

The present disclosure relates to a method obtaining an affective bandwidth measurement and affective disorder determination. The present disclosure is the first to propose the affective bandwidth concept. For example, the affective width refers to the size and range of the affective experience of a cognitive individual induced with external stimulation, including positive affective bandwidth, negative affective bandwidth and positive-negative affective bandwidth. The positive affective bandwidth refers to the size and range of the positive affective experience of the cognitive individual induced with external positive emotional stimulation; the negative affective bandwidth refers to the size and range of the negative affective experience of the cognitive individual induced with external negative emotion stimulation. The positive-negative affective bandwidth refers to the size and range of the maximum positive affective experience and the minimum negative affective experience of the cognitive individual. On the one hand, the advantage of this method is that the sizes and ranges of the positive, negative and positive-negative affective bandwidths, can be measured and on the other hand, the affective disorder of the subject can be judged and evaluated.

To this end, the technical solution of the disclosure includes the following procedures.

Affective Bandwidth Measurement.

Positive Affective Bandwidth Measurement Method:

(1-1) Selecting multiple positive pictures with a valence level higher than about 8.0 and an arousal level higher than about 5.0 according to the International Affective Picture System (IAPS);

(1-2) Selecting multiple neutral pictures with a valence level between about 4.0-5.0 and an arousal level between about 2.0-3.0 according to the IAPS;

(1-3) Processing all pictures selected in Steps (1-1) and (1-2) into pictures of the same form in terms of size, brightness and gray level using image processing software;

(1-4) Combining the multiple positive pictures processed in Step (1-3) in a non-overlapping manner to form a vision stimulation task with positive information;

(1-5) Combining the multiple neutral pictures processed in Step (1-3) together in a non-overlapping manner to form a vision stimulation task with neutral information;

(1-6) Presenting the vision stimulation of the positive pictures generated in Step (1-4) in the center of a display for 8-10 seconds of viewing, and synchronously acquiring information for all fixation points of the subject by using an eye movement tracking device;

(1-7) Presenting the vision stimulation of the neutral pictures generated in Step (1-4) in the center of a display for 8-10 seconds of viewing, and synchronously acquiring information for all fixation points of the subject using an eye movement tracking device;

(1-8) Confirming the existence of m fixation points when the subject views the positive pictures are obtained according to Step (1-6), wherein the pupil diameter mean value of each fixation point is calculated according to the following formula:

$$d_i = (d_i^{left} + d_i^{right})/2$$

$$d_P = \Sigma_1^m d_i/m$$

(i=1, 2, 3, ..., m), wherein $d_i^{left}$ and $d_i^{right}$ are the left and right pupil diameters of the $i^{th}$ fixation point, respectively;

(1-9) Confirming the existence of q fixation points when the subject views neutral pictures, wherein the mean pupil diameter value $d_M$ of each fixation point is calculated according to the formula:

$$d_k = (d_k^{left} + d_k^{right})/2$$

$$d_M = \Sigma_1^q d_k/q \quad \text{(Formula 2)}$$

(k=1, 2, 3, ..., q), wherein $d_k^{left}$ and $d_k^{right}$ are the left and right pupil diameters of the $k^{th}$ fixation point, respectively; and (1-10) Acquiring the size $S_{PaBW}$ and variation range $R_{PaBW}$ of the positive affective bandwidth (PaBW) are obtained according to Steps (1-8) and (1-9) using the following calculation:

$$S_{PaBW} = d_P - d_M$$

$$R_{PaBW} = 0 \sim (d_P - d_M) \quad \text{(Formula 3)}$$

wherein the size $S_{PaBW}(D)$ of the positive affective bandwidth of the subject and the size $S_{PaBW}(H)$ of the positive affective bandwidth of the healthy control group can be obtained.

(2) Negative affective bandwidth measurement method:

(2-1) Selecting multiple negative pictures with a valence level between about 1.0-2.0 and an arousal level higher than about 5.0 according to the IAPS;

(2-2) Processing all pictures selected in Step (2-1) into pictures of the same form in terms of size, brightness and gray level using image processing software;

(2-3) Combining multiple the negative pictures processed in Step (2-2) to form a vision stimulation task with negative information;

(2-4) Presenting the negative pictures generated in Step (2-3) in the center of the display for 8-10 seconds of viewing, and synchronously acquiring the information for all fixation points of the subject using an eye movement tracking device;

(2-5) Confirming existence of n fixation points when the subject views the negative picture are obtained according to Step (2-4), wherein the pupil diameter mean value of each fixation point is calculated according to the following formula:

$$d_j = (d_j^{left} + d_j^{right})/2$$

$$d_N = \Sigma_1^n d_j/n \quad \text{(Formula 4)}$$

(j=1,2,3, ..., n), wherein $d_j^{left}$ and $d_j^{right}$ are the left and right pupil diameters of the $j^{th}$ fixation point, respectively; and (2-6) Acquiring the size $S_{NaBW}$ and range $R_{NaBW}$ of the negative affective bandwidth (NaBW) are obtained according to Steps (2-5) and (1-9) using the following formula:

$$S_{NaBW} = d_N - d_M$$

$$R_{NaBW} = 0 \sim (d_N - d_M) \quad \text{(Formula 5)}$$

wherein the size $S_{NaBW}(D)$ of the negative affective bandwidth of the subject and the size $S^{NaBW}(H)$ of the negative affective bandwidth of the healthy control group can be obtained; and (3) Positive-negative affective bandwidth measurement method;

The positive-negative affective bandwidth (PNaBW) refers to the size and range of the maximum positive experience and the minimum negative affective experience of the cognitive individual; and the size $S_{PNaBW}$ and variation range $R_{PNaBW}$ of the positive-negative affective bandwidth (PNaBW) are obtained according to Steps (1-8) and (2-5) using the following formula;

$$S_{PNaBW} = d_P - d_N$$

$$R_{PNaBW} = d_N - d_P \quad \text{(Formula 6)}$$

wherein the size $S_{PNaBW}(D)$ of the positive-negative affective bandwidth of the subject and the size $S_{PNaBW}(H)$ of the positive-negative affective bandwidth of the healthy control group can be obtained.

Affective disorder determination method:

(2-1) Measuring the size $S_{PaBW}(D)$ of the positive affective bandwidth of the subject and the size $S_{PaBW}(H)$ of the positive affective bandwidth of the healthy control group according to Step (1);

(2-2) Measuring the size $S_{NaBW}(D)$ of the negative affective bandwidth of the subject and the size $S_{NaBW}(H)$ of the negative affective bandwidth of the healthy control group according to Step (2);

(2-3) Measuring the size $S_{PNaBW}(D)$ of the positive-negative affective bandwidth of the subject and size $S_{PNaBW}(H)$ of the positive-negative affective bandwidth of the healthy control group according to Step (3); and (2-4) Assessing the affective disorder of the subject according to the following standards: the positive affective bandwidth $S_{PaBW}(D)$ of the subject is smaller than $S_{PaBW}(H)$ of a normal person, and the positive-negative affective bandwidth $S_{PNaBW}(D)$ of the subject is smaller than $S_{PNaBW}(H)$ of the normal person; and the determination is determined using the following formula:

$$S_{PaBW}(D) < S_{PaBW}(H)$$

$$S_{PNaBW}(D) < S_{PNaBW}(H) \quad \text{(Formula 7)}$$

This method generates the following technical effects. This affective bandwidth measurement method overcomes the vagueness and uncertainty of people to a subjective scoring method for external affective experience and objectively measures the sizes and ranges (the positive affective bandwidth, the negative affective bandwidth and the positive-negative affective bandwidth) of the positive and negative affective experiences using pupil diameter as a physical index. By measuring the affective bandwidth of the subject, the defects of the previous deficiency of quantified affective evaluation are overcome, and whether the subject is affectively injured or not can be judged and evaluated compared with the normal person.

DETAILED DESCRIPTION OF THE PREFERRED EMBODIMENTS

The technical solution for this method may be further described using the attached drawings implemented in the following manner.

Figure 1:
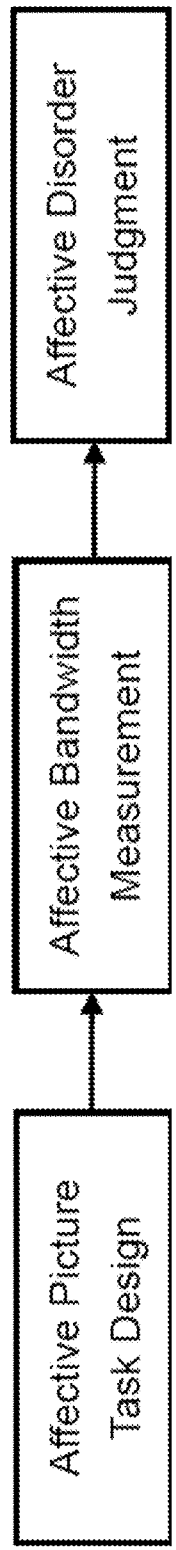
FIG. 1 is a diagram illustrating affective bandwidth measurement and disorder determination.

FIG. 1 is a diagram illustrating implementations related to affective bandwidth measurement and disorder determination. These implementations may be performed by a computing device, which may be a user device or a server. In one exemplary configuration, the computing device includes one or more processors, input/output interfaces, network interface, and memory. The memory may include various modules configured to perform the following implementations.

Figure 2:
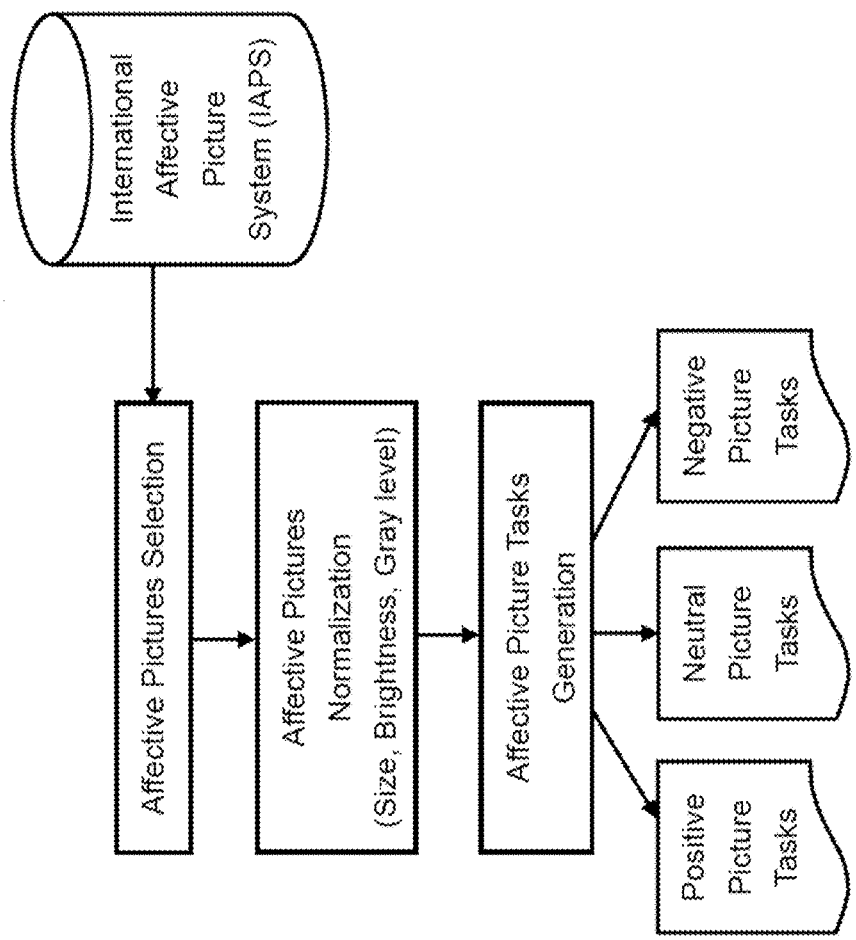
FIG. 2 is a flowchart of selecting affective pictures.

FIG. 1 includes three parts, namely, affective picture task design, affective bandwidth measurement and affective disorder determination of the depressive disorder, comprising the following procedures:

1) First, the affective picture task design shown in FIG. 2, including the following steps:

(1) Selecting 16 affective pictures from the IAPS, including four positive pictures (valence level is higher than about 8.0 and the arousal level is higher than about 5.0), four negative pictures (valence level is between about 4.0 and 5.0 and arousal level between about 2.0 and 3.0) and four neutral pictures (valence level is between about 1.0 and 2.0 and the arousal level is higher than about 5.0);

(2) Because the selected pictures are likely of different sizes, brightness and gray levels, these pictures will be normalized, and each picture will be processed into the picture of the same form in terms of size (200*200 pixels), brightness and gray level using Photoshop software; and (3) Because a certain period is needed to induce emotions from people, vision fatigue will only be induced when one picture is used to induce the emotion. Therefore, four pictures of the same form in emotion type will constitute an emotion picture task, as follows: combing the four positive pictures according to four quadrants together in a non-overlapping manner to generate a vision stimulation task with positive information; combining the four negative pictures in a non-overlapping manner according to four quadrants to generate a vision stimulation task with negative information; and combining the four neutral pictures in a non-overlapping manner according to four quadrants to generate a vision stimulation task with neutral information.

Figure 3:
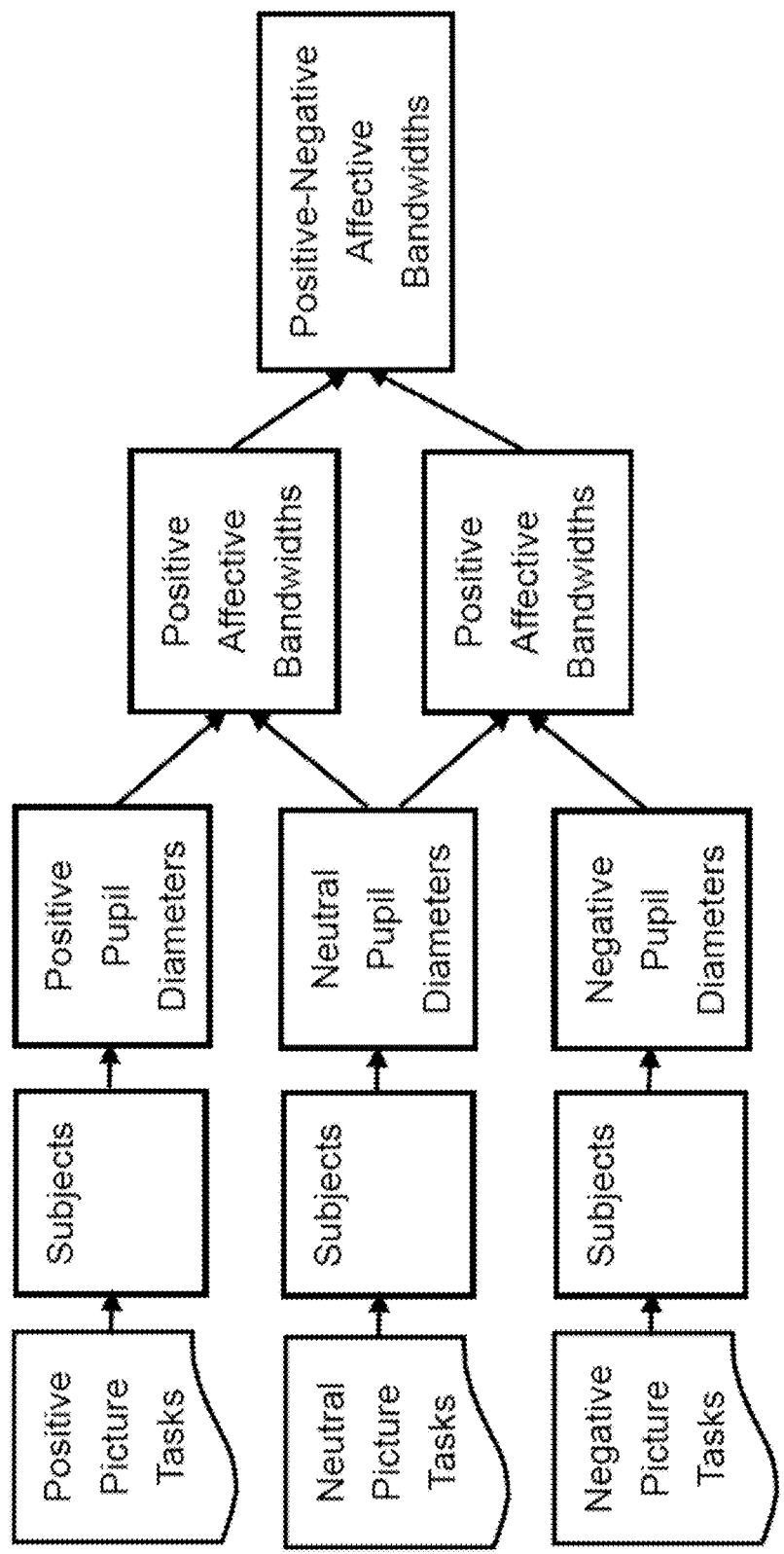
FIG. 3 is a flowchart illustrating affective bandwidth measurement.

2) Measurement of the affective bandwidth, as shown in FIG. 3, will including the following steps:

(1) Positive affective bandwidth is measured, presenting the positive affective picture task in Step 1) in the center (both the horizontal view angle and the vertical view angle are 12 degrees) of a 17-inch color display (the resolution is 1024*768) for 10 seconds of viewing and synchronously acquiring the information for all fixation points of the subject using an eye movement tracking device associated with the computing device; presenting the neutral affective picture task in Step 1) in the center (both the horizontal view angle and the vertical view angle are 12 degrees) of a 17-inch color display (the resolution is 1024*768) for 10 seconds of viewing, and synchronously acquiring the information for all fixation points using an eye movement tracking device; and presenting the negative affective picture task in Step 1) in the center (both the horizontal view angle and the vertical view angle are 12 degrees) of a 17-inch color display (the resolution is 1024*768) for 10 seconds, and synchronously acquiring the information for all fixation points using an eye movement tracking device;

(2) Pupil diameter mean value of all fixation points when the subject views the most pleasant picture is calculated:

$$d_j=(d_j^{left}+d_j^{right})/2$$

$$d_P=\Sigma_1^n d_j/m \quad \text{(Formula 1)}$$

(i=1, 2, 3, . . . , m)

wherein $d_i^{left}$ and $d_i^{right}$ are the left and right pupil diameters of the $i^{th}$ fixation point, respectively;

Similarly, the mean pupil diameters $d_N$ and $d_M$ of the subject viewing the most unpleasant picture and the neutral picture, respectively, will be calculated according to the method used in Step (2) for calculating $d_P$;

(3) The size $S_{PaBW}$ of positive affective bandwidth (PaBW) refers to the difference between the pupil diameter $d_P$ of the subject viewing the most pleasant picture and the pupil diameter $d_M$ of the subject viewing the neutral picture, and the variation range $R_{PaBW}$ of the positive affective bandwidth (PaBW) is 0 to $d_P-d_M$ according to the formula:

$$S_{PaBW}=d_P-d_M$$

$$R_{PaBW}=0 \sim (d_P-d_M) \quad \text{(Formula 3);}$$

(4) The size $S^{NaBW}$ of negative affective bandwidth (NaBW) refers to the difference between the pupil diameter $d_N$ of the subject viewing the most unpleasant picture and the pupil diameter $d_M$ of the subject viewing the neutral picture, and the variation range $R_{NaBW}$ the NaBW is 0 to $d_N-d_M$ according to the formula:

$$S_{NaBW}=d_N-d_M$$

$$R_{NaBW}=0 \sim (d_n-d_M) \quad \text{(Formula 5)}$$

(5) The PNaBW (Positive-Negative affective bandwidth) refers to the size range of the maximum positive affective experience and the size range of the minimum negative affective experience of the cognitive individual. The size $S_{PNaBW}$ and the variation range $R_{PNaBW}$ of the PNaBW are calculated according to the formula:

$$S_{PNaBW}=d_P-d_N$$

$$P_{PNaBW}=d_N-d_P \quad \text{(Formula 6)}$$

Figure 4:
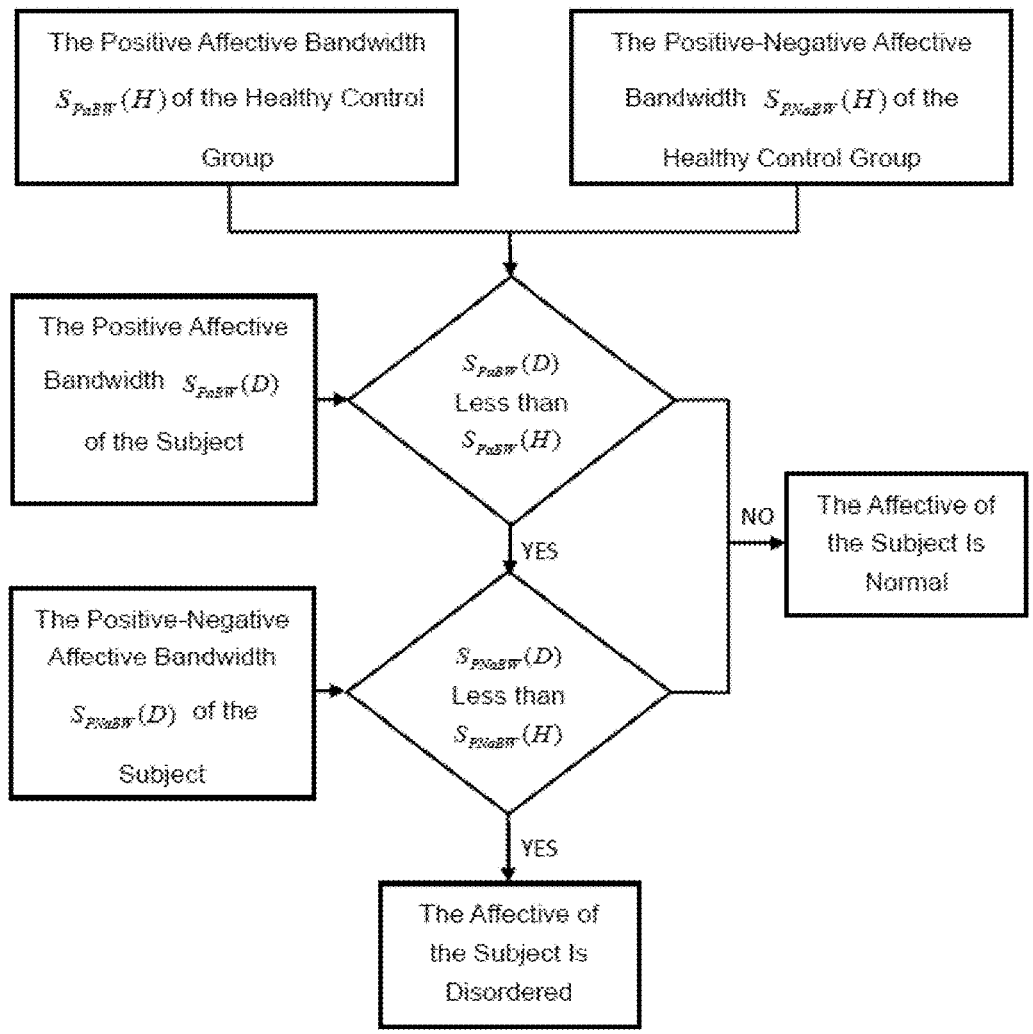
FIG. 4 is a flowchart illustrating affective disorder determination.
Figure 5:
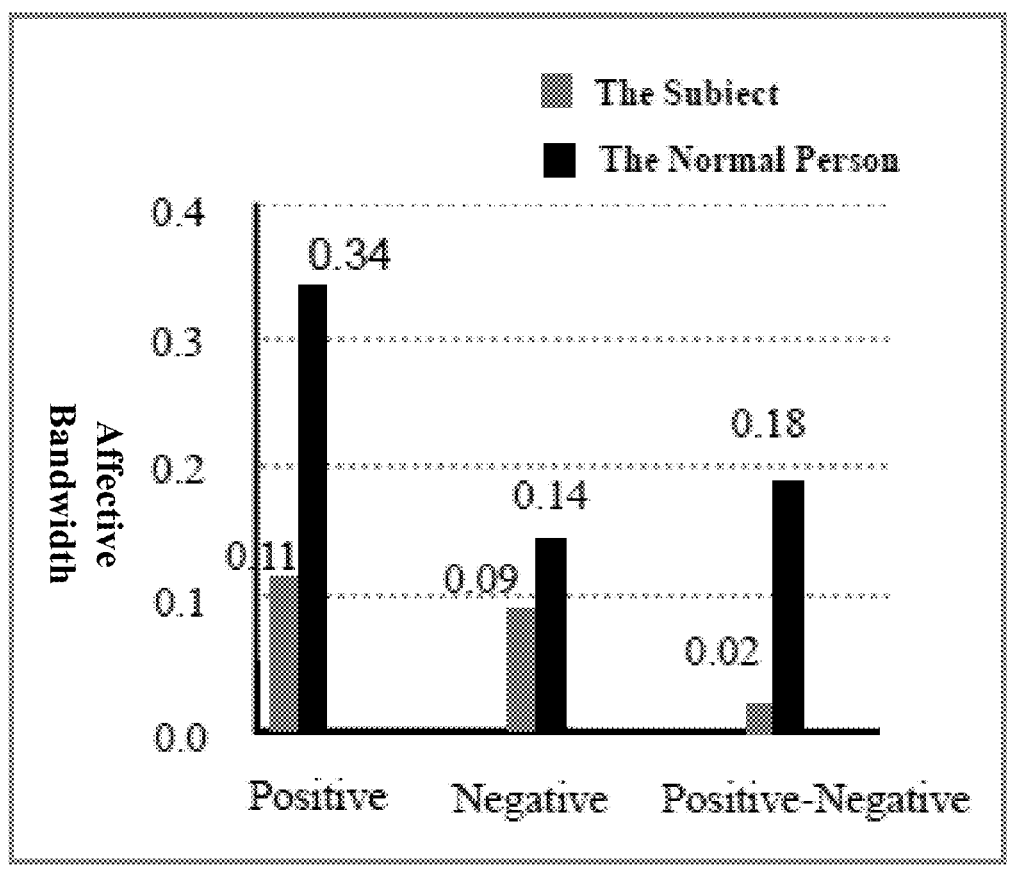
FIG. 5 is a diagram illustrating results of effective bandwidth comparison between a subject and a normal person.

3) Affective disorder determination flow, as shown in FIG. 4, will first acquire the positive affective bandwidth and the positive-negative affective bandwidth of the healthy control group; subsequently, the positive affective bandwidth and the negative affective bandwidth of the subject will be acquired; and finally, the positive affective bandwidths and the positive-negative affective bandwidths of the subject and the healthy control group will be compared. If the positive affective bandwidth of the subject is lower than that of the healthy control group and the positive-negative affective bandwidth of the subject is lower than that of the healthy control group, then the subject is depressed;

4) Evaluation of the affective disorder level of the subject;

FIG. 5 is a diagram illustrating results of effective bandwidth comparison between a subject and a normal person. FIG. 5 includes the comparison of the affective bandwidth sizes and variation ranges of 36 subjects determined as depressed according to the Beck scale and the self-rating affective disorder scale provided using implementation data obtained from the present method and the normal person. This result indicates that both the positive affective bandwidth and the positive-negative affective bandwidth of the subject are lower than those of the normal person, suggesting the positive affective experience deficiency of the subject, leading to a gloomy mood and deficiency of pleasurable feeling.

Figure 6:
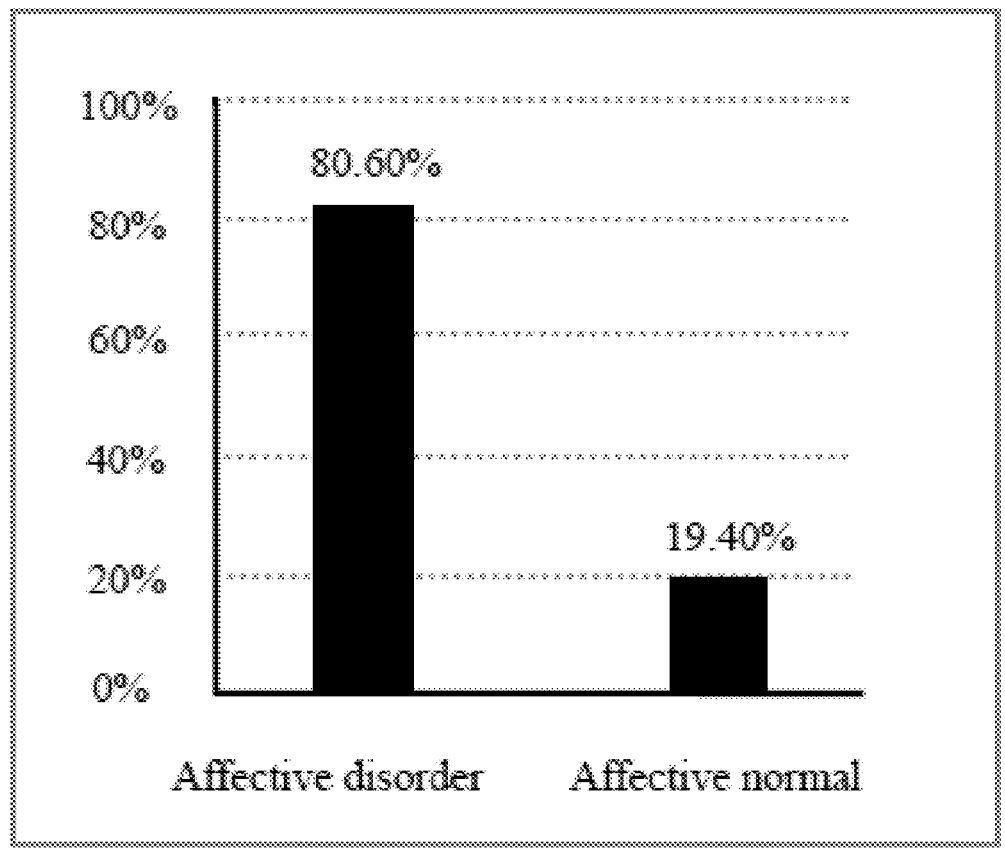
FIG. 6 is a diagram illustrating results of effective disorder determination and evaluation of a subject.

FIG. 6 is a diagram illustrating results of effective disorder determination and evaluation of a subject. The results may indicate the affective disorder assessment for the 36 subjects determined as depressed according to the Beck scale and the self-rating affective disorder scale provided using implementation data obtained from the present disclosure. The affective disorder determination and evaluation based on the affective bandwidth was obtained for 36 persons whose psychological magnitudes were assessed as depressed using the present disclosure, wherein 29 persons are evaluated as affective disorder (accounting for about 80.6%) and 7 persons are evaluated as affective normal (accounting for about 19.4%).

What is claimed is:

1. A method for measuring affective bandwidth and determining an affective disorder, the method comprising:
under control of a computing device comprising one or more processors,
measuring positive affective bandwidth of a subject by:
selecting multiple first positive pictures with a first valence level higher than about 8.0 and a first arousal level higher than about 5.0 using an International Affective Picture System (IAPS), the affective bandwidth indicating a size and a range of affective experience of the subject induced through external stimulation, the affective bandwidth including the positive affective bandwidth, negative affective bandwidth and positive-negative affective bandwidth,
selecting multiple first neutral pictures with a second valence level between about 4.0-5.0 and a second arousal level between about 2.0-3.0 using the IAPS,
normalizing the multiple first positive pictures and the multiple first neutral pictures to form a first plurality of pictures, each of the first plurality of pictures having a first size, first brightness and a first gray level,
combining the first plurality of pictures using a non-overlapping and combined together manner to void vision fatigue, thereby forming a first vision stimulation task with first positive information,
combining first neutral pictures of the first plurality of pictures in a non-overlapping and combined together manner to void vision fatigue, thereby forming a first vision stimulation task with first neutral information,
presenting first vision stimulation of the first positive pictures in a first center of a display for 8-10 seconds to the subject,
synchronously acquiring first information for fixation points of the subject using an eye movement tracking device associated with the computing device,
presenting first vision stimulation of the first neutral pictures in the center of a display for 8-10 seconds to the subject,
synchronously acquiring first information for the fixation points of the subject using the eye movement tracking device,
confirming existence of m fixation points of the fixation points when the subject views the positive pictures, wherein:
a pupil diameter mean value of each fixation point is calculated according to formula 1:

$$d_i = (d_i^{left} + d_i^{right})/2$$

$$d_p = \Sigma_1^m d_i/m \quad \text{(Formula 1)}$$

i=1, 2, 3, ..., m
$d_i^{left}$ and $d_i^{right}$ are left and right pupil diameters of a $i^{th}$ fixation point, respectively,
confirming existence of q fixation points when the subject views the first neutral pictures, wherein:
the mean pupil diameter $d_M$ of each fixation point is calculated according to formula 2:

$$d_k = (d_k^{left} + d_k^{right})/2$$

$$d_M = \Sigma_1^q d_k/q \quad \text{(Formula 2)}$$

k=1, 2, 3, ..., q,
$d_k^{left}$ and $d_k^{right}$ are the left and right pupil diameters of the $k^{th}$ fixation point, respectively, and
acquiring a size $S_{PaBW}$ and variation range $R_{PaBW}$ of the positive affective bandwidth using formula 3:

$$S_{PaBW} = d_p d_M$$

$$R_{PaBW} = 0 \sim (d_p - d_M) \quad \text{(Formula 3)},$$

wherein a size $S_{PaBW}(D)$ of the positive affective bandwidth of the subject and the size $S_{PaBW}(H)$ of the positive affective bandwidth of the healthy control group can be obtained;
measuring the negative affective bandwidth of the subject by:
selecting second multiple negative pictures with a third valence level between about 1.0-2.0 and a third arousal level higher than about 5.0 using the IAPS,
normalizing the second multiple negative pictures to form a second plurality of pictures, each of the second plurality of picture having a second size, second brightness, and a second gray level,
combining the second plurality of picture to form a second vision stimulation task with second negative information
presenting the second vision stimulation of the second multiple negative pictures in the center of the display for 8-10 seconds to the subject,
synchronously acquiring information of all fixation points of the subject using the eye movement tracking device;
confirming existence of n fixation points when the subject views the second multiple negative pictures, wherein:
a mean value of the pupil diameter $d_N$ of each fixation point is calculated using formula 4:

$$d_j = (d_j^{left} + d_j^{right})/2$$

$$d_N = \Sigma_1^n d_j/n \quad \text{(Formula 4)}$$

(j=1,2,3, ..., n)

$d_j^{left}$ and $d_j^{right}$ are left and right pupil diameters of a $j^{th}$ fixation point, respectively, acquiring the size $S_{NaBW}$ and range $R_{NaBW}$ of the negative affective bandwidth using formula 5:

$$S_{NaBW} = d_N - d_M \quad \text{(Formula 5)},$$

$$R_{NaBW} = 0 \sim (d_N - d_M)$$

obtaining the size $S_{NaBW}(D)$ of the negative affective bandwidth of the subject and size $S_{NaBW}(H)$ of the negative affective bandwidth of the healthy control group;

measuring the positive-negative affective bandwidth of the subject based on the measured the negative affective bandwidth and the measured positive affective bandwidth by:

obtaining the size $S_{PNaBW}$ and variation range $R_{PNaBW}$ of the negative affective bandwidth using formula 6:

$$S_{PNaBW} = d_P - d_N$$

$$R_{PNaBW} = d_N \sim d_P \quad \text{(Formula 6)}$$

obtaining the size $S_{PNaBW}(D)$ of the positive-negative affective bandwidth of the subject and the size $S_{PNaBW}(H)$ the positive-negative affective bandwidth of the healthy control group, the positive-negative affective bandwidth indicating a size and a range of a maximum positive affective experience and a minimum negative affective experience of the subject;

determining the affective disorder of the subject based on:

the size $S_{PaBW}(D)$ of the positive affective bandwidth of the subject and the size $S_{PaBw}(H)$ of the positive affective bandwidth of the healthy control group, the size $S_{NaBW}(D)$ of the negative affective bandwidth of the subject and the size $S_{NaBW}(H)$ of the negative affective bandwidth of the healthy control group, the size $S_{PNaBW}(D)$ of the positive-negative affective bandwidth of the subject and size $S_{PNaBW}(H)$ of the positive-negative affective bandwidth of the healthy control group using formula 7:

$$S_{PaBW}(D) < S_{PaBW}(H)$$

$$S_{PNaBW}(D) < S_{PNaBW}(H) \quad \text{(Formula 7)},$$

and determining that the subject is depressed if the positive affective bandwidth $S_{PaBW}(D)$ of the subject is smaller than $S_{PaBW}(H)$ of a standard, and the negative affective bandwidth $S_{PNaBW}(D)$ of the subject is smaller than $S_{PNaBW}(H)$ of the standard.

* * * * *